United States Patent [19]

Bedard et al.

[11] Patent Number: 4,843,007
[45] Date of Patent: Jun. 27, 1989

[54] *ALCALIGENES EUTROPHUS* FOR BIODEGRADING PCBS

[75] Inventors: Donna L. Bedard, Latham; Michael J. Brennan, Jr., Ballston Lake, both of N.Y.

[73] Assignee: General Electric Company, Schenectady, N.Y.

[21] Appl. No.: 855,274

[22] Filed: Apr. 24, 1986

[51] Int. Cl.$^4$ .......................... C12N 1/20; C12R 1/40; C12R 1/05
[52] U.S. Cl. ............................... 435/252.1; 435/262; 435/829
[58] Field of Search ............. 435/262, 253, 829, 252.1

[56] References Cited

PUBLICATIONS

Degradation of Polychlorinated Biphenyls by a Corynebacterium Species, Unterman, et al, 050, Abstracts of Annual Meeting of American Society for Microbiology, 1984, St. Louis, Missouri, Mar. 4–9, 1984.
Regulation of Polychlorinated Biphenyl Degradation in Pseudomonas Strain LB 400, L. Bopp, Q48, Abstracts of Annual Meeting of the American Society for Microbiology, 1985, Las Vegas, Nevada, Mar. 3–7, 1985.
Bacterial Isolates Exhibit Broad Differences in Extent of PCB Degradation & Congener Specificity, Unterman et al, Q58, Abstracts of Annual Meeting of American Society for Microbiology, 1985, Las Vegas, Nevada, Mar. 3–7, 1985.
Rapid Assay for Screening and Characterizing the PCB Degradative Competence of Microorganisms, Bedard et al, Q61, Abstracts of Annual Meeting of American Society for Microbiology, 1985, Las Vegas, Nevada, Mar. 3–7, 1985.
Degradation of Polychlorinated Biphenyls by *Alcaligenes eutrophus* strain H850, Bedard et al, Q51, Abstracts of Annual Meeting of American Society for Microbiology, 1984, St. Louis, Missouri, Mar. 4–9, 1984.
Biodegradation of Polychlorinated Biphenyls, TM Su, et al, Preprint Extended Abstract, American Chemical Society, New York, NY, Aug., 1981.
Bacterial Degradation of Polychlorinated Biphenyls. I., Kaiser, et al, Bulletin of Environmental Contamination & Toxicology, vol. 11, No. 3, copyright 1974, pp. 291–296.
Bacterial Degradation of Polychlorinated Biphenyls (PCB) and Their Metabolites, Furukawa, et al, Adv. Exp. Med. Biol., vol. 136A, 1982, pp. 407–418.
Growth of an Estaurine Pseudomonas sp. on Polychlorinated Biphenyl, Sayler, et al, Microbial Ecology 3, 1977, pp. 241–255.
The Degradation of Polychlorinated Biphenyls by Micro-organisms, Baxter, et al, The Science of the Total Environment, 4 (1975), pp. 53–61.
Degradation of Polychlorinated Biphenyls by Mixed Microbial Cultures, Clark, et al, Applied and Environmental Microbiology, Apr. 1979, pp. 680–685.
Effect of Chlorine Substitution on the Biodegradability of Polychlorinated Biphenyls, Furukawa, et al, Applied and Environmental Microbiology, Feb. 1978, pp. 223–227.
Metabolic Breakdown of Kaneclors (Polychlorobiphenyls) and Their Products by Acinetobacter sp., Furukawa, et al., Applied and Environmental Microbiology, Jul. 1983, pp. 140–145.
Effect of Chlorine Substitution on the Bacterial Metabolism of Various Polychlorinated Biphenyls, Furukawa, et al, Applied and Environmental Microbiology, Aug. 1979, pp. 301–310.
Biochemical and Photochemical Processes in the Degradation of Chlorinated Biphenyls, Baxter, et al, Environ. Sci. Technol, 1984, 18, pp. 608–610.
Microbial Decomposition of Chlorinated Aromatic Compounds, Rochkind, et al, IT Corporation, Knoxville, Tennessee, Contract 68-03-3074, Work Assignment 3, pp. 154–164.
Enhancement of PCBs Biodegradation by Sodium Ligninsulfonate, National Water Research Institute, Burlington, Ont., Canada, (Received Mar. 1980), D. Liu, Water Research, vol. 14, pp. 1467–1475.
Biodegradation and Detoxification of Environmental Pollutants, A. M. Chakrabarty-editor, CRC Press, Inc., Boca Raton, Florida, 1982, pp. 33–57.
Research and Development Program for the Destruction of PCBs, Third Progress Report for Jun. 1, 1983–Jun. 1, 1984, Bedard, et al, Jun. 1984, iv–v, pp. 48–87.
Microbial Degradation of Organic Compounds, David T. Gibson, editor, copyright Marcel Dekker, Inc., 1984, pp. 361–369.
Proceedings: 1983 PCB Seminar, Electric Power Research Institute, Palo Alto, Calif., Jun. 1984, pp. 4–101 through 4–117.

*Primary Examiner*—Elizabeth C. Weimar
*Assistant Examiner*—Joan Ellis
*Attorney, Agent, or Firm*—William A. Teoli; James C. Davis, Jr.; William H. Pittman

[57] ABSTRACT

A method is provided for effecting the reduction of PCB contamination in organic waste by utilizing a particular strain of a biologically pure culture of *Alcaligenes eutrophus* under aerobic conditions.

4 Claims, No Drawings

ALCALIGENES EUTROPHUS FOR BIODEGRADING PCBS

BACKGROUND OF THE INVENTION

Prior to the present invention, various techniques were developed for eliminating PCBs, or polychlorinated biphenyls from the environment. In instances where the PCBs were dissolved in an organic solvent, such as transformer oil, the contaminated solution could be treated with a mixture of polyethylene glycol and alkali metal hydroxide as shown by Brunelle, U.S. Pat. No. 4,351,718, assigned to the same assignee as the present invention and incorporated herein by reference. In many cases, the PCBs are located in more exposed environmental areas, such as landfill sites, river beds and sewage sludge. Direct chemical treatment of PCBs in such contaminated sites if often not feasible since the resulting treated solids are difficult to process further and recycle.

As shown by Colaruotolo et al., U.S. Pat. No. 4,477,570, an alternate procedure can be used for treating halogenated organic waste by effecting the removal of halogenated aromatics from the contaminated organic waste by microbial degradation. As taught by Colaruotolo et al., microorganisms have been identified having the capability of efficiently utilizing various aromatic organic chemicals as carbon sources for growth. In addition, microorganisms also have been isolated from the environment that are capable of growing in the presence of chlorinated aromatic compounds. Experience has shown, however, that PCBs found in weathered environmental soil samples, often contain five or more chlorine atoms per molecule, indicating that such polychlorinated biphenyls generally resist biodegradation.

Alternatively, as taught by J. F. Brown et al, Northeastern Environmental Science 3:167–179 (1984), PCBs in anaerobic river and lake sediments contaminated with Aroclor 1242, a PCB mixture identified further hereinafter as containing chlorobiphenyls with 2–5 chlorines per molecule or Aroclor 1254, a PCB mixture containing chlorobiphenyls with 4–7 chlorines per molecule, have undergone extensive dechlorination. The net effect of this dechlorination is the depletion of highly chlorinated biphenyls and an accumulation of mono-, di-, and trichlorobiphenyls containing 1–3 ortho chlorines. Apparently, ortho chlorines are not readily removed by the agent (presumably anaerobic bacteria) which removes meta- and para-chlorines.

The present invention is based on the discovery that certain strains of *Alcaligenes eutrophus*, identified more particularly hereinafter, have been found effective for aerobic biodegradation of PCBs having several and up to more than five chlorine atoms per molecule. Further, the *Alcaligenes eutrophus* bacteria used in the practice of the invention has also been found effective for further biodegrading dechlorinated PCBs extracted from river or lake sediment. In addition, in particular instances, metabolite resulting from the biodegradation of the PCB contaminated organic waste, can comprise cis-3,4-dihydro-3,4-dihydroxy chlorobiphenyls, ring chlorinated acetophenones, or derivatives thereof.

STATEMENT OF THE INVENTION

There is provided by the present invention, a method for biodegrading halogenated organic waste comprising PCB congeners having several and up to more than five chlorine atoms per molecule, which comprises treating the halogenated organic waste under aerobic conditions with an effective amount of biologically pure culture of *Alcaligenes eutrophus* identified as NRRLB-15940.

There is also provided by the present invention, a method for biodegrading halogenated organic waste comprising PCB congeners of the formula,

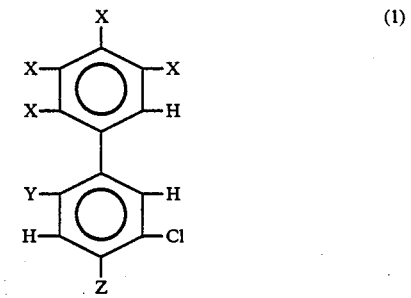

which comprises treating the halogenated organic waste under aerobic conditions with an effective amount of a biologically pure culture of *Alcaligenes eutrophus* identified as NRRLB-15940, to provide a degradation mixture comprising metabolite of the formula

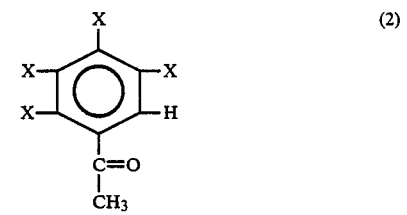

where X is chlorine or hydrogen, Y is chlorine or hydrogen and at least one of the X's or Y is chlorine, Z is hydrogen, and if Y is chlorine, Z is chlorine or hydrogen.

Some of the congeners included within formula (1) which can be treated in accordance with the practice of the present invention are, for example,

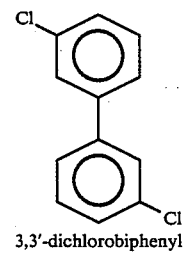
3,3'-dichlorobiphenyl

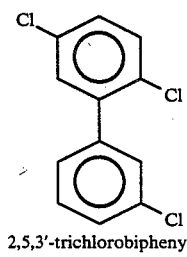
2,5,3'-trichlorobiphenyl

-continued

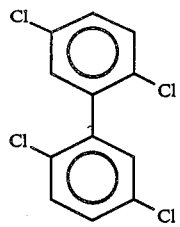

2,5,2',5'-tetrachlorobiphenyl

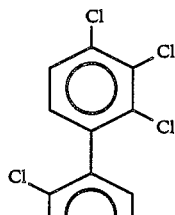

2,3,4,2',5'-pentachlorobiphenyl

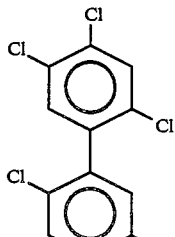

2,4,5,2',5'-pentachlorobiphenyl

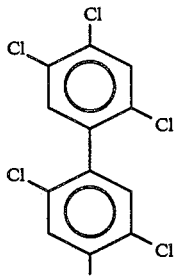

2,4,5,2',4',5'-hexachlorobiphenyl

Among the ring-chlorinated acetophenones which can be formed in accordance with the practice of the method of the present invention as shown by formula (2) are, for example,

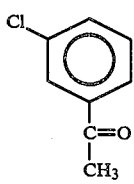

3'-chloroacetophenone

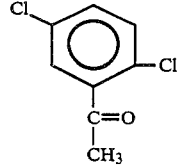

2'5'-dichloroacetophenone

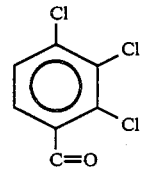

2',3',4'-trichloroacetophenone

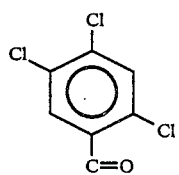

2',4',5'-trichloroacetophenone

PCBs have been used widely in industrial applications because of their thermal stability, excellent dielectric (electrically insulating) properties, and resistance to oxidation, acids, bases, and other chemical agents. Complex mixtures of PCBs were marketed under the tradename Aroclor (Monsanto Company, USA).

The PCBs have been released into the environment for many years and are a worldwide contaminant. They are lipophilic and sorb strongly to the lipids and fats of animals including fish, mussels, and birds. PCBs also undergo biological magnification in such common aquatic invertebrates as daphnids, mosquito larvae, stoneflies, and crayfish. The concentration of PCBs in the invertebrates can be as high as 27,500 times that in water. As these invertebrates are subsequently eaten by fish and birds, bioaccumulation occurs at all levels of the food chain.

As used hereinafter, the term "Aroclor 12XX" indicates a commercial mixture of chlorinated biphenyls, where the digits indicated by XX correspond to the weight percent chlorine in the molecule. Accordingly, Aroclor 1242 is 42% chlorine by weight, averages 3 chlorines per molecule, and contains some molecules having five or more chlorines per molecule.

A culture of the bacterium *Alcaligenes eutrophus* used in the practice of the present invention, referred to hereinafter as "H850" is on deposit with the U.S. Department of Agriculture as (NRRLB-15940). A progeny of the subject microorganism will be provided by the assignee of this application under the conditions imposed by 37 CFR 1.114 and 35 USC 122 in the event that the Commissioner of Patents and Trademarks determines that an individual is entitled to same.

Upon issuance of the subject application as a patent, subculture of this strain can be obtained from the permanent collection of the Agricultural Research Culture Collection (NRRL) at the Northern Regional Research Center, U.S. Department of Agriculture, Peoria, Ill., U.S.A.

The taxonomic identification of H850 was made and it was found to be a mixture of two colony types: the colonies of one type were smooth, entire, mucoid, whereas those of the second type were compact, pulvinate and wrinkled. Some of the physiological and biochemical characteristics of H850 were found to be as follows:

| Characteristic | H850 | Characteristic | H850 |
|---|---|---|---|
| Gram negative | + | D-glucose as SCS* | − |
| Motile at 37° C. | + | lactose as SCS | − |
| Motile at RT | + | maltose as SCS | − |
| Flagella peritrichous | + | D-mannitol as SCS | − |
|  |  | L-rhamnose as SCS | − |
| 4° C. growth | − | D-ribose as SCS | − |
| 25° C. growth | + | D-sorbitol as SCS | − |
| 30° C. growth | + | sucrose as SCS | − |
| 37° C. growth | + | trehalose as SCS | − |
| 41° C. growth | − | D-xylose as SCS | − |
| Pyocyanine produced | − | adonitol as SCS | − |
| Fluorescein produced | − | erythritol as SCS | − |
| Melanin pigment produced | − | glycerol as SCS | + |
|  |  | ethanol as SCS | + |
| pH 6.0 growth | + | geraniol as SCS | − |
| 3% NaCl growth | − | i-inositol as SCS | − |
| 6.5% NaCl growth | − | sebacic acid as SCS | + |
| MacConkey agar growth | + | acetamide as SCS | − |
|  |  | DL-α-aminovalerate as SCS | − |
| Skim milk agar growth | + | DL-α-adipate as SCS | + |
| Aesculin hydrolysis | − |  |  |
| Testosterone degradation | + | DL-α-benzoate as SCS | + |
| Starch hydrolysis | − |  |  |
| Gelatinase | − | DL-α-butyrate as SCS | + |
| Tween 20 hydrolysis | − |  |  |
| Tween 80 hydrolysis | − | DL-α-citraconate as SCS | + |
| Indole | − |  |  |
| Simmons citrate | + | D-gluconate as SCS | + |
| growth |  | M-hydroxybenzoate as SCS | + |
| Urease | + |  |  |
| Nitrate to nitrite | + | D-fructose as SCS | + |
| Nitrite reduction | − | 2-ketogluconate as SCS | + |
| Nitrite to nitrogen gas | − |  |  |
|  |  | L-arabinose as SCS | − |
| L-tryptophan | − | Casein hydrolysis | − |
| cellobiose as SCS | − | DL-lactate as SCS | + |
| Hydrogen sulfide (TSI) | − | malate as SCS | + |
|  |  | pelargonate as SCS | + |
| Lysine decarboxylase | − |  |  |
| Arginine (Mollers) | − | propionate as SCS | + |
| Ornithine decarboxylase- | − |  |  |
|  |  | quinate as SCS | + |
| Arginine hydrolysis | − | succinate as SCS | + |
| Phenylalanine deamination | − | L-+-tartrate as SCS | + |
|  |  | valerate as SCS | + |
| Lecithinase | − | β-alanine as SCS | + |
| Phosphatase | + | D-α-alanine as SCS | + |
| Catalase | + | betaine as SCS | − |
| Oxidase | + | glycine as SCS | + |
| Gluconate oxidation | − | L-histidine as SCS | + |
| Growth on malonate as SCS | + | DL-norleucine as SCS | + |
|  |  | L-proline as SCS | + |
| Tyrosine degradation | + | D-tryptophan as SCS | − |
| dl-hydroxybutyrate growth | + | L-valine as SCS | + |
|  |  | DL-arginine as SCS | − |
| PHB accumulation | + | benzylamine as SCS | − |
| Deoxyribonuclease | − | butylamine as SCS | − |
| Growth on 0.05% cetrimide | − | putrescine as SCS | − |
|  |  | mesoconate | + |
| Growth on acetate as SCS | + | DL gylcerate | + |

*SCS = sole carbon source

In the practice of the invention, H850 can be used to biodegrade halogenated organic waste which hereinafter means contaminated soil from landfill sites, river beds, leachates therefrom, and aqueous surfactant solution resulting from washing the aforementioned organic waste to transfer the PCBs to the aqueous surfactant solution. One method of treating the organic waste is by inoculating or reintroducing H850 to the contaminated environment. For example, the bacteria can be dispersed onto a landfill site under aerobic conditions in nutrient medium. Biodegradation can be monitored to determine the effectiveness of the treatment.

Surfactants which can be used in the practice of the present invention to wash PCB contaminated organic waste are, for example, Surco 233, a sodium salt of an alkylenebenzene sulfonate made by the ONYX Chemical Co. of Jersey City, NJ.

In order that those skilled in the art will be better able to practice the present invention, the following examples are given by way of illustration and not by way of limitation. All parts are by weight.

EXAMPLE 1

A mixed bacterial culture was obtained from a sample of PCB-contaminated soil obtained from a dredge site located near Lock 7-5A of the Hudson River. Approximately 5 g of the PCB contaminated soil was placed in 50 ml of a phosphate-buffered minimal salts medium containing biphenyl as a carbon source and supplemented with 0.005% yeast extract. The phosphate-buffered minimal salts medium was prepared by adding 77.5 ml of a buffered salt concentrate and 50 mg of yeast extract to 910 ml of glass distilled water. The salt concentrate consisted of 56.77 g/l of $K_2HPO_4$, $KH_2PO_4$ (21.94 g/l), and $NH_4Cl$ (27.61 g/l). After autoclaving and upon cooling 10 ml of additional salts consisting of $MgSO_4$ (19.5 g/l), $MnSO_4.H_2O$ (5 g/l), $FeSO_4.H_2O$ (1 g/l), and $CaCl_2.2H_2O$ (0.3 g/l) were added along with several drops per liter of concentrated $H_2SO_4$ to prevent precipitation of basic salts. Biphenyl was supplied by the addition of sterile, molten biphenyl to the autoclaved medium.

Cultures were incubated aerobically at 30° C. in a gyratory shaker. After incubating for at least three days, the sediment was allowed to settle and 1 ml of the broth was transferred to a second flask containing fresh medium. When growth was apparent, the culture was transferred a third time. After the third transfer, the mixed culture, designated H8, was maintained by continuous transfer to fresh biphenyl medium at intervals of 7-21 days.

The H8 was then diluted with medium and plated on Luria agar. Approximately 20 colonies, including all colonies which differed in colonial morphology were picked. Colonies judged to be pure on the basis of microscopic examination after gram staining were inoculated into the above-described biphenyl phosphate-buffered minimal salts medium. Pure cultures capable of utilizing biphenyl as a sole carbon and energy source were again plated out onto Luria agar. In each case, a single colony of the pure culture was selected. Part of the colony was used to inoculate biphenyl/phosphate-buffered broth to establish a stock culture. The remainder of the colony was tested for a gram reaction and characterized using the N/F system (Flow Laboratories, Inc.) Six different colonies were isolated and characterized on the basis of the gram reaction, motility, morphology and the 17 parameters of the N/F system. The purity of each of the six isolates was confirmed by gram stain and macroscopic examination of colonies. The strains were identified as slightly different strains of *Alcaligenes eutrophus,* an aerobic, facultatively chemolithotrophic, hydrogen-oxidizing bacterium commonly found in soil, mud, and water. The six strains were found to have identical PCB-degradative competence, and one was selected for further studies, hereinafter identified as "H850".

H850 cells were grown to an optical density of 1.0 at 615 nm, then filtered to remove biphenyl crystals and washed twice with a 0.05 molar solution of sodium phosphate buffer (pH 7.5). The cells were resuspended in the buffer and separated into 1 ml aliquots. There was added to each H850 aliquot, 10 µl of a 0.5 mM solution (in acetone) of 1,4,5,2',4',5'-hexachlorobiphenyl and 10 µl of a 0.5 mM solution (in acetone) of 3,5,3',5'-tetrachlorobiphenyl (an internal standard). The final concentration of each PCB congener was 5 micromoles/liter. The mixtures were then incubated in a gyratory incubator for 72 hours at 30° C. under sealed conditions. The cells were then killed by the addition of perchloric acid to a final concentration of 0.7% or by heating at 70° C. for 20 minutes.

The entire contents of the vials were extracted by the following procedure. One tenth volume of 10% Triton X-100 was added to the cell suspensions to facilitate the quantitative recovery of PCBs and metabolites. A small amount of anhydrous sodium sulfate was added to each sample to prevent formation of a stable emulsion and then each sample was then extracted with 4 volumes of hexane. During extraction the samples were shaken vigorously for 20–30 minutes in a horizontal position on a reciprocating platform shaker. The phases separated rapidly without centrifugation. The samples were then analyzed on a Hewlett-Packard 5880 GC equipped with an automatic sampler, an electron capture detector and a glass column packed with 1.5% SP2250/1.95% SP2401 on 100/120 Supelcoport. Samples were chromatographed using a temperature program which began at 150° C., then was raised to 220° C. at 5° per minute and held at 220° C. for 20 minutes. Nitrogen was used as a carrier gas at a flow rate of 60 ml per minute. It was found that about 93% (4.6 nmol) of the 2,4,5,2',4',5'-hexachlorobiphenyl had been degraded in 72 hours. In addition, approximately 0.28 nmol or about 6% of the degraded PCB had been converted to 2',4',5'-trichloroacetophenone. These results indicate that the H850 of the present invention is capable of degrading hexachlorobiphenyls, including those with blocked 2,3 and 3,4 positions, and in providing a metabolite of a trichloroacetophenone.

EXAMPLE 2

The procedure of Example 1 was repeated except that several additional PCB congeners were utilized as substrates for the H850 organism. The following results were obtained.

TABLE I

| PCB Congener | PCB Congener Concentration (µM) | Minimum Length of Incubation (hours) | Extent of Degradation % | Chloroacetophenone Produced |
|---|---|---|---|---|
| 2,5,2' | 45 | 24 | 97 | 2' |
| 2,3,2',5' | 25 | 24 | N.D. | 2',3'* |
| 2,5,2',5' | 45 | 2 | 24 | 2',5'* |
| 2,5,3',4' | 5 | 24 | 88 | 3',4' |
| 2,3,4,2',5' | 5 | 24 | 95 | 2',3',4'* |
| 2,4,5,2',5' | 45 | 24 | 70 | 2',5' and 2'4'5'* |
| 2,4,5,2',4',5' | 5 | 72 | 93 | 2',4'5'* |
| 3,3' | 45 | 15 | 50 | 3' |
| 2,5,3' | 45 | 24 | 96 | 2',5' |
| 3,4,3' | 45 | 48 | N.D. | 3',4' |

N.D. = not determined
*verified by GCMS

The above results show that the H850 organisms of the present invention are effective for degrading a variety of PCBs and generating chloroacetophenone metabolite therefrom. It was found that approximately 1.8 nmol of 3'-chloroacetophenone was generated from the degradation of 30.6 nmol of 3,3'-dichlorobiphenyl in 15 hours. Hence, there was a yield of about 5.9% of the corresponding chloroacetophenone from the degraded PCB. For all other congeners, except 2,4,5,2',4',5', less than 1 nanomole of the appropriate chloroacetophenone accumulated. (This corresponds to less than 1% of the degraded PCB). In most instances, however, it was further found that the H850 can metabolize the chloroacetophenones to unknown products.

EXAMPLE 3

H850 cells were grown at 30° C. with shaking in a minimal salts medium (Stanier et al, 1966) supplemented with either sodium succinate (0.2%) and yeast extract (0.005%) or casamino acids (0.2%).

Biphenyl (0.2%) was added at the early log phase of growth and cells were harvested, washed, and resuspended in potassium phosphate buffer (50 mM, pH 7.5). Resting-cell suspensions were incubated with 2,5,2',5'-tetrachlorobiphenyl (3–10 mg) for 2 to 24 h. Cultures were subsequently acidified to pH 1.5–2.0 and extracted with ethyl acetate. The extract was dried and the residues resuspended in methanol and analyzed by HPLC on a component system consisting of a Waters model 6000A solvent-delivery system, a model U-6K septumless injector, and a model 440 absorbance detector operated at 254 nm. The metabolites of 2,5,2',5'-tetrachlorobiphenyl were separated on an Ultrasphere-ODS 5µ column with a linear gradient of acetonitrile-acetic acid (1%) in water (50–95%). As the products eluted, samples were collected and analyzed by UV spectrophotometry, mass spectrometry, an proton magnetic resonance. Based on these and further analyses a metabolite was identified as cis-3,4-dihydro-3,4-dihydroxy-2,5,2',5'-tetrachlorobiphenyl.

EXAMPLE 4

The procedure of Example 1 was repeated except that the cells were incubated with a mixture in the presence of mixtures containing 9 or 10 congeners, each at a concentration of 5µM, which further contain Surco 233, at a concentration of 0, 0.5% by volume or 2% by volume. The cells were incubated with the PCBs for 24 hours in the presence or absence of Surco 233. The PCBs were then extracted with four volumes of hexane and aliquots were analyzed by chromatographing isothermally at 190° C. on a Hewlett Packard 5880 GC. The results obtained are shown in Table II below.

TABLE II

| | Percent Degradation | | |
|---|---|---|---|
| PCB Congener | No Surfactant | 0.5% Surco 233 | 2.0% Surco 233 |
| 2,4' | 100 | 100 | 100 |
| 4,4' | 73 | 0 | 0 |
| 2,4,4' | 86 | 15 | 0 |
| 2,5,2',5' | 100 | 96 | 59 |
| 2,3,2',5 | 100 | 96 | 60 |
| 2,3,2',3' | 100 | 99 | 50 |
| 2,4,3',4' | 0 | 0 | 0 |
| 2,4,5,2',3' | 35 | 12 | 0 |
| 3,4,3',4' | 0 | 0 | 0 |
| 2,4,5,2',4',5' | 0 | 0 | 0 |
| 2,2' | 100 | 100 | 100 |
| 2,3 | 100 | 100 | 99 |
| 2,5,2' | 100 | 100 | 100 |
| 2,5,4' | 100 | 99 | 94 |
| 2,4,2',4' | 88 | 28 | 8 |
| 2,5,3',4' | 100 | 97 | 58 |
| 2,4,5,2',5' | 100 | 72 | 23 |
| 2,3,4,2',5' | 100 | 65 | 18 |
| 2,4,5,2',4',5' | 0 | 0 | 0 |

The above results show that the H850 cells of the present invention can be used to degrade a variety of PCBs having up to 5 chlorine atoms per molecule in the presence of up to 2% by volume of a surfactant.

EXAMPLE 5

A. eutrophus H850 cells were prepared and incubated as described in Example 1. 10 microliters of a 1000 ppm solution of Aroclor 1242 (in acetone) was added to 1 ml of cells to give a final concentration of 10 ppm. The length of the incubation was 48 hours. The sample was analyzed on a Varian vista 4600 gas chromatograph equipped with an electron capture detector and splitter/injector, both operated at 330° C., using a fused silica capillary column. The carrier gas and makeup gas were helium (30 cm/second) and nitrogen (25 ml/minute), respectively. Samples were chromatographed using a temperature program which was held at 40° C. for 2 minutes, then raised to 80° C. at 10° C./minute, then to 225° C. at 6°/minute and held at 225° C. for 10 minutes. Injections (1 microliter) were done by the splitless technique, using a vent-time of 0.9 minutes. After a 48 hour incubation period, a comparison was made between Aroclor 1242 treated with heat-killed cells and living cells of A. eutrophus H850. It was found that H850 was very effective in biodegrading commercial PCBs having 1-5 chlorine atoms per molecule.

EXAMPLE 6

The procedure of Example 4 was repeated, except that in place of Aroclor 1242, there were used Aroclor 1242 samples extracted from Hudson River sediment which had undergone partial dechlorination under anaerobic conditions. A comparison was made between sample incubated with heat-killed H850 cells for 48 hours and samples incubated with active H850 cells for 48 hours. The chromatograph showed that H850 substantially degraded PCB congeners having two or more orthochlorines (e.g. 2,2'-; 2,6,3'-; 2,6,2'-; and 2,3,6-chlorobiphenyls), which were generated in high quantities by the anaerobic dechlorination process.

EXAMPLE 7

The procedure of Example 1, was repeated except that in place of the 2,4,5,2',4',5'-hexachlorobiphenyl, the washed H850 cells were incubated with 0.1 g/ml of a variety of PCB/soil formulations. The PCB spiked soil was prepared by treating PCB-free soil with Aroclors. One sample contained 50 ppm of Aroclor 1242, while another sample contained 50 ppm Aroclor 1254. Additional PCB-laden soil samples were prepared containing 500 ppm of Aroclor 1242. An environmental sample (from South Glen Falls, NY) containing 525 ppm of Aroclor similar to Aroclor 1248 was also evaluated.

PCB reductions found after 2-3 days, as calculated from GC area depletion, were at least 70% for the 50 ppm Aroclor 1242 samples, 50% for the 500 ppm Aroclor 1242 samples, 43% for the 50 ppm Aroclor 1254, and 20% for the 525 ppm South Glen Falls environmental sample.

Although the above examples are directed to only a few of the very many variables which can be used in the practice of the method of the present invention, it should be understood that the method of the present invention is directed toward a broader variety of PCB congeners, substrates contaminated with such PCB congeners, and conditions used in the treatment of PCB contaminated substrates with H850 in accordance with the practice of the method of the present invention.

What is claimed is:

1. A biologically pure culture of *Alcaligenes eutrophus* having the identifying characteristics of *Alcaligenes eutrophus*, NRRLB-15940, said characteristics including the ability to degrade polychlorinated biphenyls to provide a degradation mixture comprising a member selected from the class consisting of bis-3,4-dihydro-3,4-dihydroxychlorobiphenyls, ring-chlorinated acetophenones, and derivatives thereof.

2. A biologically pure culture of *Alcaligenes eutrophus* in accordance with claim 1 having the ability to degrade PCB congeners with blocked 2,3 positions.

3. A biologically pure culture of *Alcaligenes eutrophus* in accordance with claim 1 having the ability to degrade PCB congeners with blocked 2,3 and 3,4 positions.

4. A biologically pure culture of *Alcaligenes eutrophus* in accordance with claim 1 having the ability to degrade PCB congeners having the formula

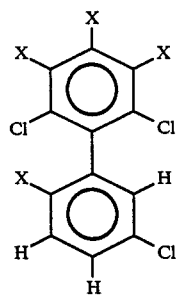

where X is chlorine or hydrogen.

* * * * *